United States Patent [19]

Nipper

[11] Patent Number: 4,997,438
[45] Date of Patent: Mar. 5, 1991

[54] PRESSURE APPLICATOR FOR THORACIC WOUNDS

[75] Inventor: John Nipper, North Fort Myers, Fla.

[73] Assignee: Constance Crane Langmann, Ft. Myers, Fla.

[21] Appl. No.: 337,914

[22] Filed: Apr. 14, 1989

[51] Int. Cl.⁵ .............................................. A61B 17/12
[52] U.S. Cl. ..................................... 606/201; 606/204
[58] Field of Search ................ 606/201, 202, 203, 204

[56] References Cited

U.S. PATENT DOCUMENTS

| | | | |
|---|---|---|---|
| 1,252,260 | 1/1918 | Gilberg | 606/203 |
| 1,338,578 | 4/1920 | Maeda | 606/201 |
| 2,185,571 | 1/1940 | Robinson | 606/203 |
| 2,271,927 | 2/1942 | Saighman | 606/203 |
| 3,628,536 | 12/1971 | Glesne | 606/203 |
| 3,756,239 | 9/1973 | Smythe | 606/202 |
| 3,874,387 | 4/1975 | Barbieri | 606/201 |
| 4,175,562 | 11/1979 | Honan | 606/202 |
| 4,182,338 | 1/1980 | Stanulis | 606/203 |
| 4,308,861 | 1/1982 | Kelly | 606/204 X |
| 4,427,007 | 1/1984 | Rekroth | 606/201 |

Primary Examiner—Robert A. Hafer
Assistant Examiner—Michael Brown
Attorney, Agent, or Firm—William E. Noonan

[57] ABSTRACT

A pressure applicator for thoracic wounds is disclosed. The device includes a strap for encircling a patient's thorax. The strap has a pair of opposing ends. A cup element is attachable to the strap and has a rim for engaging the paatients's thorax around the wound. The strap is selectively secured in place about the thorax to urge the cup element against the thorax with sufficient pressure to at least partially seal the wound.

9 Claims, 2 Drawing Sheets

PRESSURE APPLICATOR FOR THORACIC WOUNDS

FIELD OF THE INVENTION

This invention relates to a pressure applicator for thoracic wounds, and more particularly, to an applicator for treating sucking chest wounds and other injuries to the thorax.

BACKGROUND OF INVENTION

Serious wounds to the chest or other areas of the thorax are attributable to various causes such as gun shots, stabbing and automobile accidents. Because so many vital organs, such as the heart and lungs, are located within the chest cavity, wounds in this area are very often quite serious and require prompt and effective medical attention. Sucking chest wounds are particularly dangerous. When an opening is created in the chest cavity, the desired internal and external pressure balance is lost and the lungs may partially or fully collapse. This is often accompanied by excessive blood loss from internal organs and blood vessels. Accordingly, it is vital that emergency medical personnel take quick and appropriate action to prevent lung collapse and excessive blood loss.

Presently, most chest wounds are treated with various types of bandages and tourniquets. Most often, gauze is applied to the wound and held in place by tape. However, vaseline or a similar substance is typically applied to the gauze and as a result, this technique is very messy and often ineffective because the lubricating material tends to interfere with the adhesion of the tape. Moreover, this apparatus is also ineffective in preventing lung collapse.

SUMMARY OF THE INVENTION

Therefore, it is an object of the present invention to provide a pressure applicator that effectively treats thoracic wounds by sealing the wound to reduce blood loss and prevent lung collapse.

It is a further object of this invention to provide a pressure applicator that is adjustable for wounds in various locations about the thorax and for various size patients.

It is a further object of this invention to provide a pressure applicator that may be applied quickly and effectively at the site of an injury or in an ambulance or other emergency vehicle.

It is a further object of this invention to provide a pressure applicator that is not messy and remains securely fixed to the patient after it is applied.

This invention results from the realization that improved sealing of sucking chest wounds may be achieved by providing a virtual vacuum above the wound and that such a vacuum may be created by urging a suction cup against the thorax and around the wound.

This result is achieved by the present invention which features a pressure applicator for thoracic wounds, including a strap for encircling a patient's thorax. The strap has a pair of opposing ends. A cup element is attachable to the strap and has a rim for engaging the patient's thorax around the wound. There are means for selectively securing the strap in place about the thorax to urge the cup element against the thorax with sufficient pressure to at least partially seal the wound.

In a preferred embodiment, the strap is elastic and includes a plurality of holes arranged longitudinally in the strap. The cup element may include at least one knob that is formed proximate the base of the cup element and is receivable by a selected one of the holes to attach the cup to the strap. The knob may have a diameter that is larger than the holes and the holes may be resiliently expandable to introduce the knob through and remove the knob from a selected hole.

The cup may be composed of a generally soft, flexible material. It may have a generally circular shape, or, alternatively, a generally oblong shape.

The means for securing may include first and second hook elements that are attached proximate respective ends of the strap. Each hook element is engagable with a selected, respective one of the holes to secure the strap in place. Alternatively, various other hook and loop, button and snap elements may be employed to secure the strap in place about the patient.

Other objects, features and advantages of the invention will become apparent from the following detailed description of the preferred embodiments with reference therein to the accompanying drawings.

A BRIEF DESCRIPTION OF THE DRAWINGS

DETAILED DESCRIPTION OF PREFERRED EMBODIMENT

Figure 1:
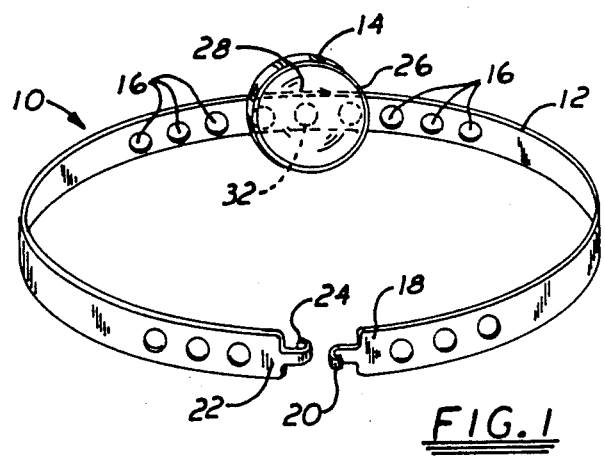
FIG. 1 is a perspective view of the pressure applicator of this invention.

There is shown in FIG. 1 a pressure applicator 10 for treating sucking chest wounds and other types of wounds to the thorax. Applicator 10 includes an elongate, elastic strap 12 and a generally hemispheric shaped cup element 14 that is attached to strap 12.

Figure 2:
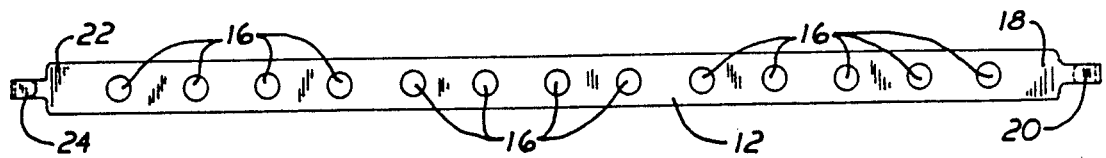
FIG. 2 is a plan view of the elastic strap that is employed by the pressure applicator.

Strap 12, shown alone in FIG. 2, is preferably composed of rubber or various synthetic elastomeric materials. The elasticity of strap 12 enables it to be wrapped around the human thorax and adjusted in length to fit various chest sizes. A plurality of holes 16 are formed longitudinally along strap 12. Holes 16 optionally may be provided with reinforced openings in the form of grommets or similar means. However, such reinforcement is not required. First end 18 of strap 12 includes an outwardly facing hook 20 and second end 22 includes a similar inwardly facing hook 24. Hooks 20 and 24 selectively engage respective holes 16 in a manner described more fully below, so that the ends of the strap may be fastened to secure strap 12 in place about a patient's thorax. Various alternative means that may be employed to fasten strap 12 include hook and loop (Velcro) fasteners, buttons and snaps.

Figure 3:
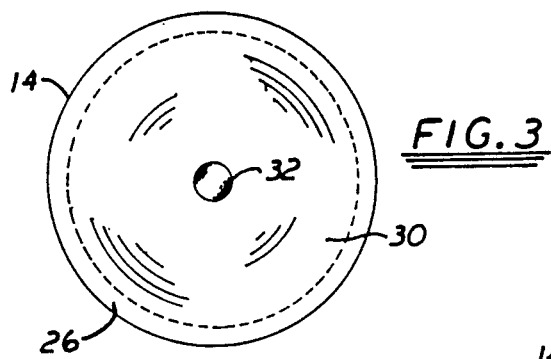
FIG. 3 is a plan view of the cup element.
Figure 4:
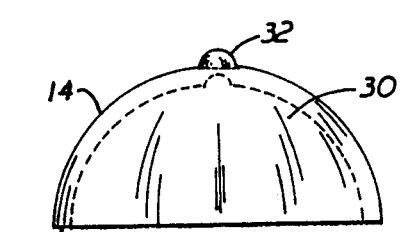
FIG. 4 is an elevational view of the cup element in FIG. 3.

Cup element 14, shown alone in FIGS. 3 and 4, is preferably formed from a generally soft, flexible material such as rubber or a soft plastic. The cup element includes a rim 26 that surrounds its cavity or opening 28. The outside of cup element 14 includes a base 30. A nipple or knob 32 is formed integrally on the outside surface of cup element 14 proximate base 30.

Figure 5:
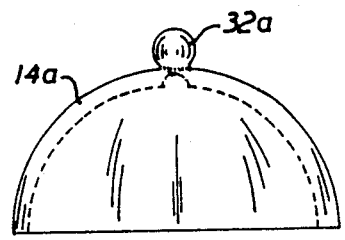
FIG. 5 is an elevational view of a cup element employing an alternative knob.
Figure 6:
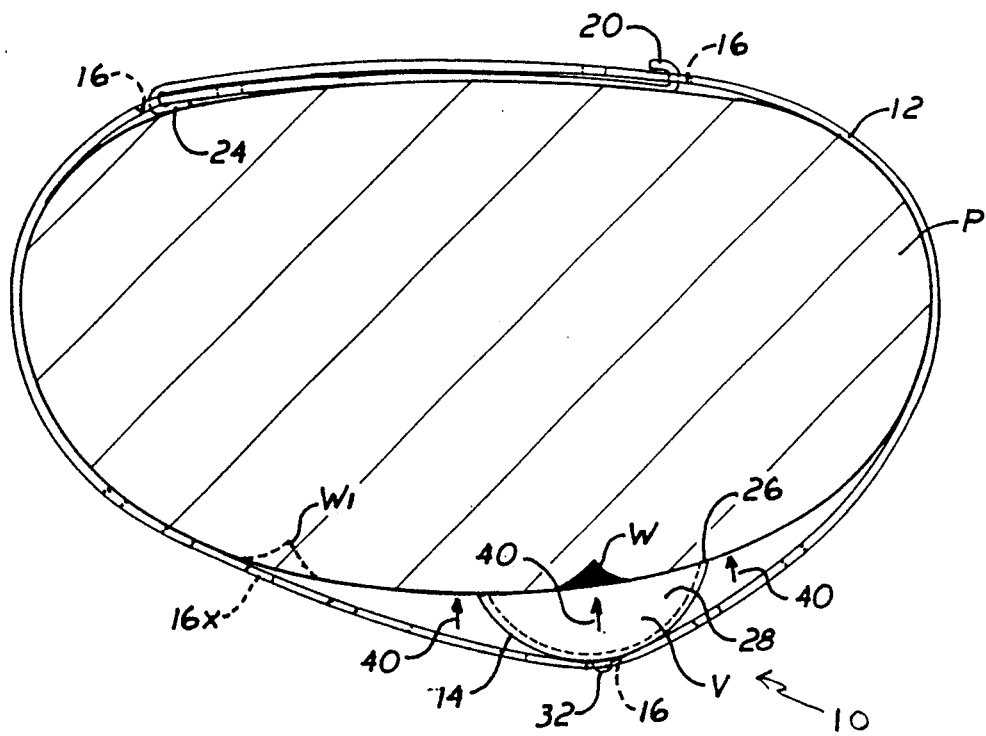
FIG. 6 is a plan view of the pressure applicator as applied to a patient having a chest wound, the patient being shown in section.

Cup element 14 is selectively attached to a desired position on strap 12 by introducing knob 32 through a selected hole 16, in the manner shown most clearly in FIG. 6. Typically, knob 32 has a diameter which is slightly larger than the diameter of opening 16 when the strap is in its relaxed condition. The strap is stretched so that hole 16 expands and knob 32 is introduced through the hole 16 from the inside of strap 12. An alternative cup 14a, FIG. 5, includes a knob 32a with a somewhat different shape. The diameter of knob 32a is even larger than the holes 16 to provide a more secure attachment of cup element 14 to strap 12. Again, the holes are resiliently expanded by stretching the strap so that the knob 32a may be fit through a selected hole, thereby attaching cup element 14 to strap 12.

Applicator 10 is employed, as shown in FIG. 6, to apply pressure to a chest wound W in patient P. Strap 12 is wrapped about patient P such that cup element 14 is disposed above wound W with the rim 26 of the cup element engaging patient P and encircling wound W. Strap 12 is stretched and attached by securing hook elements 20 and 24 through respective strap holes 16. Various selected holes 16 are shown in phantom in FIG. 6. The number, spacing and location of these holes may be varied as needed. The appropriate holes 16 are selected so that the strap 12 exerts sufficient tension to urge cup element 14 inwardly against the patient's chest in the direction of arrows 40. Rim 26 tightly engages the patient's chest around wound W and this causes the cup element to effectively seal the wound. As cup element 14 is urged inwardly in this manner, it operates as a suction cup. A virtual vacuum V is created within the cavity 28 of the cup element. As a result, the proper pressure balance is maintained inside and outside of the patient's chest. External pressure is prevented from entering through wound W and collapsing the lung. At the same time, excessive blood loss is stemmed. Accordingly, applicator 10 seals wound W until patient P is transported to a facility where the wound can be properly treated and stitched. Applicator 10 is removed simply by releasing hook elements 20 and 24 from the respective strap holes 16.

The plurality of holes 16 in strap 12 provides a number of benefits. Cup element 14 may be adjusted longitudinally along strap 12 and positioned to cover a wound at various alternative locations in the thorax. For example, cup element 14 may be attached to strap 12 at hole 16x so that it may be engaged with a wound W1. The multiple holes 16 also permit a plurality of cup elements 14 to be simultaneously engaged with respective holes if the patient exhibits multiple wounds and each wound requires a respective cup element. Moreover, the multiple holes permit the hook elements 20 and 24 to be attached where needed to provide a desired strap tension. That tension may vary for patients having various chest sizes and applicator pressure requirements.

Figure 7:
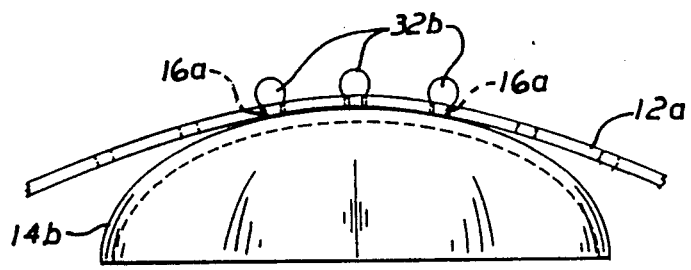
FIG. 7 is an elevational view of an alternative, oblong cup element that may be used in accordance with this invention.

An alternative cup element 14b is disclosed in FIG. 7. Cup element 14b includes a generally oblong shape which permits it to effectively seal large or irregularly shaped wounds. Due to its larger oblong shape, cup element is provided with multiple knobs 32b that are fastened to strap 12a through holes 16a. In all other respects, cup element 14b functions analogously to the previously described cup element. Multiple cup elements having various shapes may be stored in the emergency vehicle so that emergency personnel may select an appropriate cup element for treating a particular type of wound. All such cup elements are interchangeably attachable to a single strap that is adjustable in size as described above.

Although specific features of the invention are shown in some of the drawings and not others, this is for convenience only, as each feature may be combined with any and all of the other features in accordance with this invention.

Other embodiments will occur to those skilled in the art and are within the scope of the following claims:

What is claimed is:

1. A pressure applicator for thoracic wounds comprising:
    a flexible cup element that is substantially and permanently impervious to fluid flow therethrough, said cup element having an open cavity for facing a thoracic wound and a rim for engaging the patient's thorax around the wound;
    a strap for completely encircling the patient's thorax and extending over and across said cup element, said strap having attachment menas engaging a portion of said cup within said rim, said strap having a pair of opposing ends; and
    means for selectively securing said strap in place about the thorax to urge said cup element against said thorax with sufficient pressure to create at least a partial vacuum within said cavity to at least partially seal the wound.

2. The applicator of claim 1 in which said strap includes a plurality of holes arranged longitudinally in said strap.

3. The applicator of claim 2 in which said cup element includes at least one knob that is formed proximate the base of said cup element and is receivable by a selected one of said holes to attach said cup element to said strap.

4. The applicator of claim 3 in which said knob has a diameter that is larger than said holes and in which said strap is elastic such that said holes are resiliently expandable to introduce said knob through, and remove said knob from said holes.

5. The applicator of claim 1 in which said cup element is composed of a generally soft, flexible material.

6. The applicator of claim 1 in which said cup element includes a generally hemispheric shape.

7. The applicator of claim 1 in which said cup element includes a generally oblong shape.

8. The applicator of claim 1 in which said means for securing includes first and second hook elements that are attached proximate respective said ends of said strap, each said hook element being engagable with a respective one of said holes to secure said strap in place.

9. The applicator of claim 1 in which said strap is longitudinally elastic.

* * * * *